(12) United States Patent
Oeltgen et al.

(10) Patent No.: US 6,316,411 B1
(45) Date of Patent: Nov. 13, 2001

(54) PROTECTION AGAINST ISCHEMIA AND REPERFUSION INJURY

(75) Inventors: Peter R. Oeltgen, Winchester, KY (US); Paul D. Bishop, Fall City, WA (US); Mark S. Kindy; Juan A. Sanchez, both of Lexington, KY (US)

(73) Assignees: University of Kentucky Research Foundation, Lexington, KY (US); ZymoGenetics, Seattle, WA (US)

( * ) Notice: Subject to any disclaimer, the term of this patent is extended or adjusted under 35 U.S.C. 154(b) by 0 days.

(21) Appl. No.: 09/477,100

(22) Filed: Jan. 4, 2000

(51) Int. Cl.$^7$ .................................................. A61K 38/00
(52) U.S. Cl. .............................. 514/13; 530/326; 530/300
(58) Field of Search .............................. 514/13; 530/326, 530/300

(56) References Cited

PUBLICATIONS

Bolling et al., The use of hibernation induction triggers for cardiac transplant preservation, Transplantation 63: 326–329, 1997.
Bolling et al., Delta opioid agonist/antagonist activity and ischemic tolerance, American Heart Association Meeting, Atlanta, GA, Nov., 1999.
Bolling et al., Use of "natural" hibernation induction triggers for myocardial protection, Annals Thorac. Surg.: 623–627, 1997.
Chien et al., Two–day preservation of major organs with autoperfusion multiorgan preparation and hibernation induction trigger, J. Thorac. Cardiovasc. Surg., 102: 224–234, 1991.
Chien et al., Extension of tissue survival time in multiorgan block preparation with a delta opioid DADLE (D–Ala2, D–Leu5)–enkephalin), J. Thorac. Cardiovasc. Surg., 107: 965–967, 1994.
Stanley M. Crain and Ke–Fei Shen, Antagonists of excitatory opiod receptor functions enhance morphine's analgesic potency and attenuate opioid tolerance/dependence liability, Pain 82 (1999), 1–11.
Fryer et al., Opioid–induced cardioprotection against myocardial infarction and arrhythmias: Mitochondrial versus sarcolemmal ATP–sensitive potassium channels, JPET 294: 451–457, 2000.
Kevelaitis et al., Opening of potassium channels: The common cardioiprotective link between perconditioning and natural hibernation?, Circulation 99: 3079–3085, 1999.
Lishmanov et al., Activation of the $\mu$–opioid receptors as a factor increasing heart resistance against ischemic and reperfusion damages, Russian J. Physiol. 1998; 84 (11) (Russian w/ attached English translation).
L.N. Maslov and Yu. B. Lishmanov, Effects of $\mu$– and delta opioid receptor ligands on rhythm and contractility disorders of isolated rate heart in postischemic period, Kardiologya 1998; 12: 25–30 (Russian w/ English translation).

Oeltgen et al., The use of delta–2 opioid agonists for myocardial ischemia protection, Abstract, Experimental Biology 2000, submitted Nov., 1999.
P.R. Oeltgen et al., Extended lung preservation with the use of hibernation trigger factors, Ann. Thorac. Surg. 61: 1488–93, 1996.
Schultz et al., Evidence for involvement of opiod receptors in ischemic preconditioning in rat hearts, Am. J. Physiol. 268 (Heart Circ. Physiol. 3): H2157–H2161, 1995.
M.D. Schwartz et al., Delta opioid receptors and low temperature myocardial protection, Ann. Thorac. Surg. 68: 2089–92, 1999,
C.F. Toombs et al., Limitation of infarct size in the rabbit by ischaemic preconditioning is reversible with glibenclamide, Cardio. Res. 27: 617–622, 1993.
Wu et al., Delta opioid extends hypothermic preservation time of the lung, J. Thorac. Cardiovasc. Surg. 1996; 111: 259–267.
G.M. Zhao and H.N. Bhargava, Effects of multiple intracerebroevntricular injections of [D–Pen2, D–Pen5] enkephalin and [D–Ala2, Glu4] deltorphin II on tole4rance to their analgesic actoin and on brain $\delta$–opiod receptors, Brain Research: 745 (1997) 243–247.
Bolling et al., Hibernation triggers and myocardial protection, Circulation 98: 11220–11223, 1998.
Fryer et al., Opioid–induced second window of cardioprotection: Potential role of mitochondrial K–ATP channels, Circ Res. 1999; 84: 846–851.
K.P. Mayfield and L.G. D'Alecy, Delta–1 opioid receptor dependence of acute hypoxic adaptation, J. Pharmacol. Exp. Ther. 268: 74–77, 1994.
J.E. Schultz et al., Ischemic preconditioning in the intact rat heart is mediated by $\delta$ 1– but not $\mu$ or $\kappa$–opioid receptors, Circ 97: 1282–1289, 1998.
Schultz et al., Morphine mimics the cardioprotective effect of ischemic preconditioning via a glibenclamide–sensitive mechanism in the rat heart, Circ. Research. 78: 1100–1104, 1996.
R. Schulz et al., Involvement of activation of ATP–dependent potassium channels in ischemiec preconditioning in swine, Am. J. Physiol. 267: H1341–1352, 1994.
Stefano et al., Delta–2 opioid receptor subtype on human vascular endothelium uncouples morphione stimulated nitric oxide release, International J. Cardiology 64: Suppl. 1, S43–S51, 1998.
D.M. VanWinkle et al., Cardioprotection provided by adenosine receptor activation is abolished by blockade of the K–ATP channel, Am. J. Physiol. 266: H829–H839, 1994.

*Primary Examiner*—Karen Cochrane Carlson
(74) *Attorney, Agent, or Firm*—Wood, Herron & Evans, L (57) ABSTRACT

A compound and method for using the compound to reduce injury associated with ischemia and reperfusion of mammalian organs such as the heart. The compound may be administered as part of a preconditioning strategy which reduces the extent of injury and improves organ function following cessation and restoration of blood flow. The compound may be used in preparation for planned ischemia or in a prophylactic manner in anticipation of further ischemic events.

24 Claims, 4 Drawing Sheets

SEQUENCE LISTING

```
<160> NUMBER OF SEQ ID NOS: 1

<210> SEQ ID NO 1
<211> LENGTH: 17
<212> TYPE: PRT
<213> ORGANISM: XYZ
<220> FEATURE:
<221> NAME/KEY: PEPTIDE
<222> LOCATION: (0)...(0)
<221> NAME/KEY: MOD_RES
<222> LOCATION: (1)...(0)
<223> OTHER INFORMATION: Xaa = D-Leu

<400> SEQUENCE: 1

Tyr Xaa Phe Ala Asp Val Ala Ser Thr Ile Gly Asp Phe Phe His Ser
 1               5                  10                  15

Ile
```

PROTECTION AGAINST ISCHEMIA AND REPERFUSION INJURY

FIELD OF THE INVENTION

The invention relates to compounds protective against ischemia and reperfusion injury, particularly in the myocardium, and their use.

BACKGROUND

Tissues deprived of blood and oxygen undergo ischemic necrosis or infarction with possible irreversible organ damage. In some circumstances, however, such as during cardiac surgery, it is desirable to interrupt the normal myocardial contractions (cardioplegia) and actually induce ischemia. Such elective or obligatory ischemia occurs in the presence of safeguards such as cardioplegia-induced cardiac arrest and hypothermia. While these safeguards provide considerable myocardial protection, alteration of myocardial energetics (stunning) and poor postoperative ventricular function still remain significant problems.

Once the flow of blood and oxygen is restored to the organ or tissue (reperfusion), the organ does not immediately return to the normal preischemic state. Reperfused postischemic non-necrotic myocardium is poorly contractile and has reduced concentrations of high energy nucleotides, depressed subcellular organelle function and membrane damage that resolves only slowly. Although reperfusion restores oxygen and reverses ischemia, repletion of high energy nucleotides such as adenosine triphosphate (ATP) and reversal of ischemic membrane damage is slow, and contractile function may be profoundly depressed for a long period. Just minutes of ischemia causes loss of myocardial systolic wall thickening for hours. Longer periods of reversible ischemia may depress contractility for days. Studies confirm that, despite restoration of myocardial flow and a quick recovery of myocardial oxygen consumption ($MVO_2$) following ischemia, there is only very slow recovery of myocardial contractile function. The problems are exacerbated in high risk patients, such as those with poor preoperative ventricular function, recent myocardial infarction or left ventricular hypertrophy. These same problems also occur during organ storage for cardiac transplant, under which there are time constraints due to the limits of myocardial preservation.

Postischemic dysfunction may be due to a variety of factors. Oxygen free radicals may play a role, as generation of free radicals in stunned myocardium has been demonstrated and free radical scavengers have been shown to attenuate contractile dysfunction. Impaired intracellular calcium handling and calcium overload during early reperfusion may contribute to postischemic dysfunction; while calcium infusions enhance contractility in both normal and postischemic myocardium, ischemia as short as a few minutes produces an impairment in sarcoplasmic reticulum calcium transport and a shift of the calcium ATPase activity. Postischemic myocardium is also associated with reduced concentrations of myocardial high-energy phosphates and adenine nucleotides, as obligatory reduction in myocardial ATP content during ischemia occurs as myocytes utilize ATP for maintenance of cellular integrity. Since ATP is essential for myocardial contraction and relaxation, ATP depletion may have detrimental effects upon postischemic myocardial functional recovery.

The high volume of cardiac-related surgeries, both elective and emergency procedures and including cardiac transplants, lead to the above-described problems. Thus, methods and agents to provide protection against myocardial ischemia and to avoid post ischemic dysfunction are needed.

SUMMARY OF THE INVENTION

The invention is directed to an agent and a method of using the agent to reduce the injury associated with ischemia and reperfusion of organs such as the heart. The compound is Tyr-D-Leu-Phe-Ala-Asp-Val-Ala-Ser-Thr-Ile-Gly-Asp-Phe-Phe-His-Ser-Ile-$NH_2$ SEQ ID NO:1, hereinafter compound-D. Administration of compound-D SEQ ID NO:1, particularly prior to an ischemic event, reduces tissue necrosis and preserves organ function.

In one embodiment, a method of protecting against ischemia and reperfusion injury in a mammal is disclosed. An effective concentration of compound-D SEQ ID NO:1 is administered to the mammal in a pharmaceutically acceptable formulation prior to the onset of ischemia, for example, 24 hours prior to ischemia. In other embodiments, compound-D SEQ ID NO:1 is administered substantially concurrent with the onset of ischemia, during an ischemic episode, or post-ischemia. The formulation may be administered parenterally at a concentration in the range of about 1–20 mg/kg of body weight.

The invention is also directed to a method to prevent damage to an isolated organ, for example, a heart for transplant. The isolated organ is exposed to a preservative solution containing an effective amount of compound-D SEQ ID NO:1. The concentration of compound-D SEQ ID NO:1 in the preservative solution for a heart is about 100 $\mu$M.

The invention is additionally directed to a method for reducing effects of an ischemic episode in a mammal by administering an effective concentration of compound-D SEQ ID NO:1 in a pharmaceutically acceptable carrier. Administration is prior to or substantially concurrently with the onset of ischemia, or one hour post cerebral ischemia.

The invention is further directed to a composition that protects a mammalian organ from injury. The composition contains compound-D SEQ ID NO:1. Compound-D may be naturally occurring or may be synthesized.

The invention is also directed to an organ preservative solution that contains compound-D at a concentration effective to protect the organ, such as a heart, from ischemic injury.

These and other advantages of the invention will be apparent in light of the following drawings and detailed description.

DETAILED DESCRIPTION

The invention is directed to a compound that has a salutary effect on cardiac function following ischemia, and methods of using the compound. The compound may be administered directly to an individual, and is particularly effective when administered 24 h prior to the onset of ischemia. This may occur, for example, prior to scheduled cardiac surgery. The compound may also be included in a preservative solution for an isolated organ, such as a heart or liver being maintained viable for transplant.

The compound is a peptide having the sequence Tyr-D-Leu-Phe-Ala-Asp-Val-Ala-Ser-Thr-Ile-Gly-Asp-Phe-Phe-His-Ser-Ile-NH$_2$ SEQ ID NO: 1, hereinafter referred to compound-D. The peptide may be produced by a number of methods, such as using an automated peptide synthesizer, through recombinant molecular techniques, or isolated from a naturally occurring source, as is known to one skilled in the art. Compound-D SEQ ID NO:1 has a molecular weight of 1,902 daltons. Compound-D SEQ ID NO:1 is insoluble in water or saline, but may be solubilized by adding 100 $\mu$M of a solution comprised of ethanol, propylene glycol, and 1 N NaOH in a 1:1:1 ratio, with sterile physiological saline then used to obtain the appropriate concentration. The initial alkaline pH is adjusted to 7.4 with 1 N HCl.

Compound-D SEQ ID NO:1 that has been solubilized may be administered by parenteral means, for example, by intravenous injection. In one embodiment, administration of compound-D SEQ ID NO:1 is at the time of induced ischemia, but may also be added during or even after an ischemic event. For administration into a mammal, a dose of about 1–20 milligrams per kilogram (mg/kg) is useful. For administration into a tissue or organ preservation solution, a concentration of about 100 $\mu$M is useful.

Compound-D SEQ ID NO:1 may be administered directly into a mammal, either alone or in combination with other substances. Alternatively, it may be added as a component of a solution used to maintain the viability of isolated organs, such as an additive to cardioplegia and other organ preservation solutions. In one embodiment, compound-D SEQ ID NO:1 is coadministered as an adjuvant with other compounds or strategies that are designed to protect organs from ischemia. As an example, compound-D SEQ ID NO:1 may be administered with agents that affect nitric oxide (NO) synthase, such as arginine hydrochloride. Arginine hydrochloride is known to prevent the decline in cardiac function following an ischemic episode.

The following description demonstrates use and efficacy of compound-D SEQ ID NO:1 in a variety of systems.

PERFUSED HEART

Compound-D SEQ ID NO:1, at a dose of 2 mg/kg and solubilized as described above, was administered by tail vein injection into rats weighing between about 350–400 g (number of animals (n)=6). Control rats (n=6) were injected in the same manner with an equal volume of 0.9% NaCl. After 24 h, the hearts from both treated and control animals were excised and perfused in a modified Langendorff perfusion apparatus at 37° C. using oxygenated Krebs-Henseleit buffer as the perfusate, as known to one skilled in the art. Coronary perfusion pressure was maintained at 70 mm Hg by regulating coronary flow. All hearts were paced at 5.5 Hz (300 beats per minute, bpm) except during ischemia. A saline-filled balloon was inserted in the left ventricle to measure developed pressure (DP) and end-diastolic pressure (EDP) in mm Hg. After 15 min equilibration, both groups were subjected to 20 min zero-flow global ischemia, and then were reperfused for 120 min.

Left ventricles were isolated and divided into three segments along their short axis, stained with triphenyltetrazolium chloride, and stored in formalin. Infarct size was measured on digitized images and expressed as a per centage of myocardium. Data were expressed as mean plus or minus standard error of the mean (±SEM) and were analyze using a paired Student's t-Test. Confidence limits were established at 95%.

Figure 1:
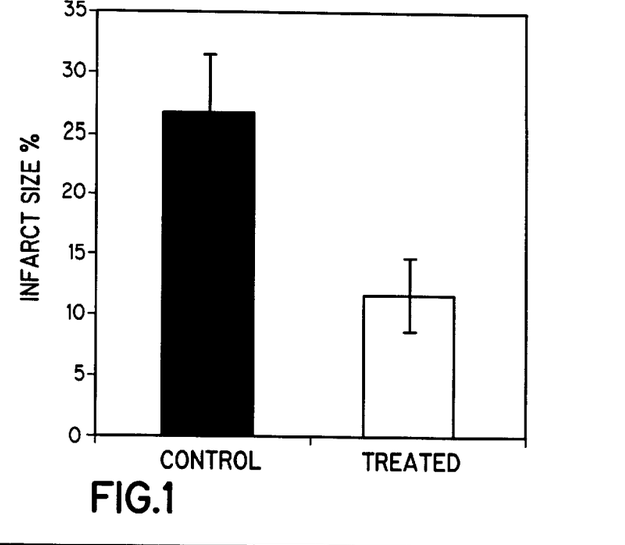
FIG. 1 is a histogram showing myocardial infarction size in control and treated animals.

The results are shown in FIG. 1, which is a histogram of the infarct size in hearts from both animals receiving only saline (control, solid bar) and in animals treated with compound-D SEQ ID NO:1 at 2.0 mg/kg (treated, open bar) 24 h prior to 20 min ischemia and 120 min reperfusion. Pretreatment of animals with compound-D SEQ ID NO:1 significantly decreased the percent of infarct size (p<0.05). Control rats had a mean infarct size of 27±5%, while rats pretreated with compound-D had a reduced mean infarct size of 12±3%.

Figure 2:
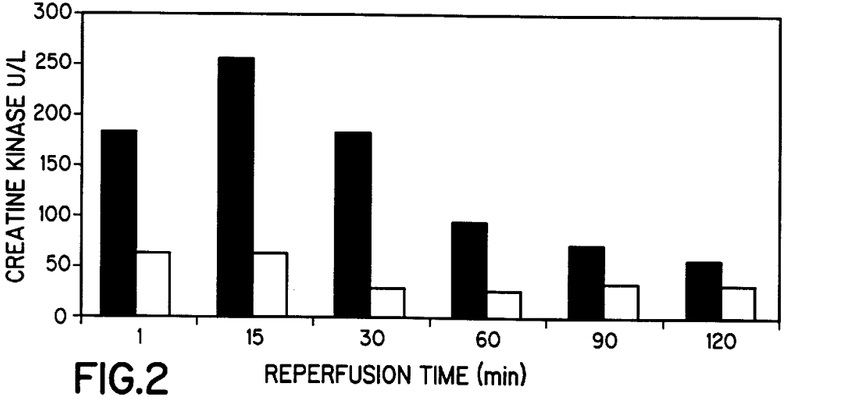
FIG. 2 is a histogram showing post-ischemic release of creatine kinase in control and treated animals.
Figure 3:
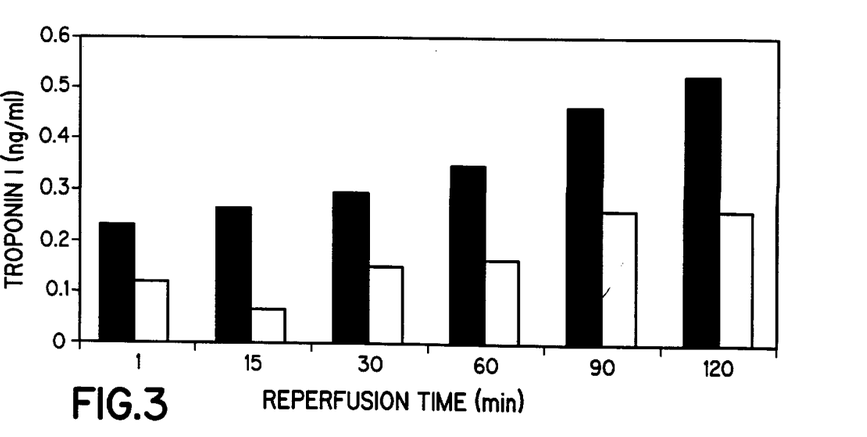
FIG. 3 is a histogram showing post-ischemic release of troponin I in control and treated animals.

Compound-D SEQ ID NO:1 pretreatment also significantly decreased total creatine kinase (CK) and the cardiac form of troponin I (cTn–1) values following 20 min ischemia, as shown in FIGS. 2 and 3, respectively. CK is an enzyme that is normally found in muscles such as the heart (that is, in myocytes), but is released during severe muscle trauma such as occurs in a myocardial infarction. Thus, measurement of CK is an indicator of the degree of muscle damage or trauma. Similarly, cTn–1 is a protein associated specifically with cardiac muscle, and an increase in cTn–1 indicates myocardial damage.

FIG. 2 is a histogram showing CK released during reperfusion of isolated rat hearts after 20 min ischemia in rats treated 24 h prior to ischemia with 2.0 mg/kg compound-D SEQ ID NO:1. The solid bars represent control animals (n=6) and the open bars represent treated animals (n=6). FIG. 3 is a histogram showing cTn–1 released during reperfusion of isolated rat hearts after 20 min ischemia in rats treated 24 h prior to ischemia with 2.0 mg/kg compound-D SEQ ID NO:1. The solid bars represent control animals (n=6) and the open bars represent treated animals (n=6). At each time point during reperfusion where samples were collected for CK and cTn–1 analysis (1, 1 5, 30, 60, 90 and 120 min reperfusion), CK levels in control rats were higher than CK levels in treated rats, and Tn–1 levels in control rats were higher than Tn–1 levels in treated rats. This indicated that pretreatment with compound-D SEQ ID NO:1 decreased the damage to the myocardium, as compared to animals that did not receive compound-D SEQ ID NO:1.

Figure 4:
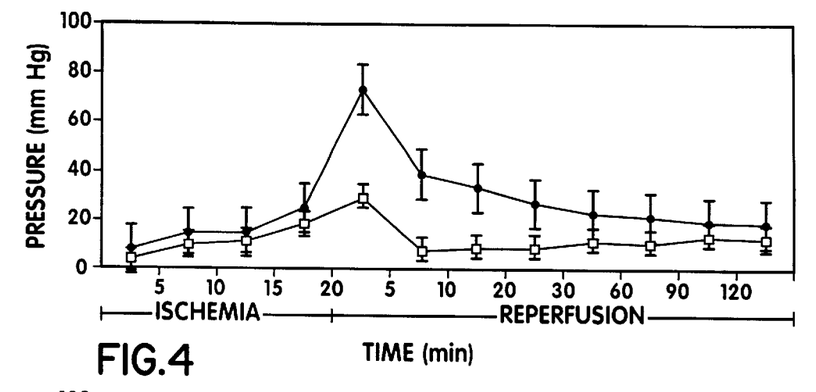
FIG. 4 is a graph showing end diastolic pressure in the left ventricle of control and treated animals.
Figure 5:
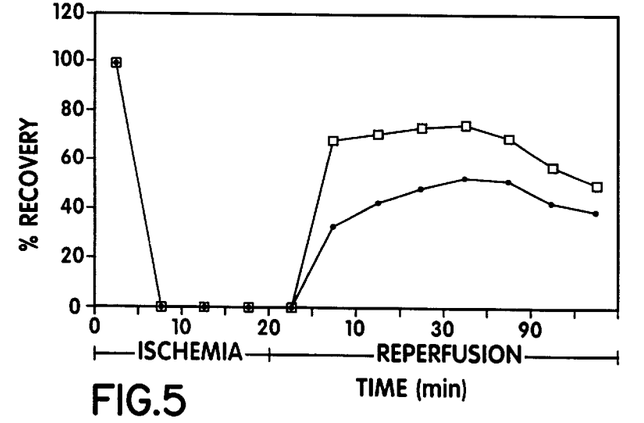
FIG. 5 is a graph showing functional recovery in control and treated animals.
Figure 6:
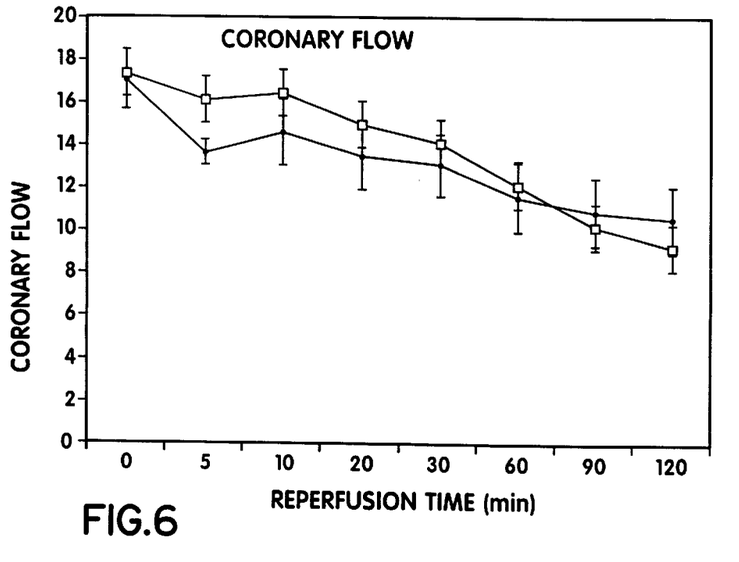
FIG. 6 is a graph showing coronary flow in control and treated animals.

Compound-D SEQ ID NO:1 pretreatment also resulted in improved postischemic ventricular function. FIG. 4 is a graph of end diastolic pressure (EDP) in mm/Hg in the left ventricle during reperfusion of isolated rat hearts after 20 min ischemia in rats treated 24 h prior to ischemia with 2.0 mg/kg compound-D SEQ ID NO:1. Open squares are from treated animals, and solid circles are from control animals. FIG. 5 is a graph showing percent of functional recovery during reperfusion of isolated rat hearts after 20 min ischemia in rats treated 24 h prior to ischemia with 2.0 mg/kg compound-D SEQ ID NO:1. Open squares are from treated animals, and solid circles are from control animals. Differences in recovery of developed pressure (DP) of compound-D SEQ ID NO:1 treated hearts remained statistically significant to 90 min following initiation of reperfusion, as shown in FIG. 4, and in end diastolic pressure to 20 min following initiation of reperfusion, as shown in FIG. 5. Left ventricular functional recovery (% recovery of baseline preischemic developed pressure during reperfusion) was markedly improved in treated animals (open squares) compared to control animals (solid circles) to 90 min of reperfusion. As shown in FIG. 6, coronary flow was not significantly different between control animals (solid circles) and compound-D SEQ ID NO:1 treated animals (open squares).

These results show that in a normoxic, isolated perfused rat heart preparation, administration of compound-D can confer cardioprotection when administered 24 h prior to planned ischemia. The salutary effects on the post-ischemic myocardium include reduced infarct size, decreased release of both creatine kinase and cardiospecific troponin 1, and improved ventricular performance.

Figure 7:
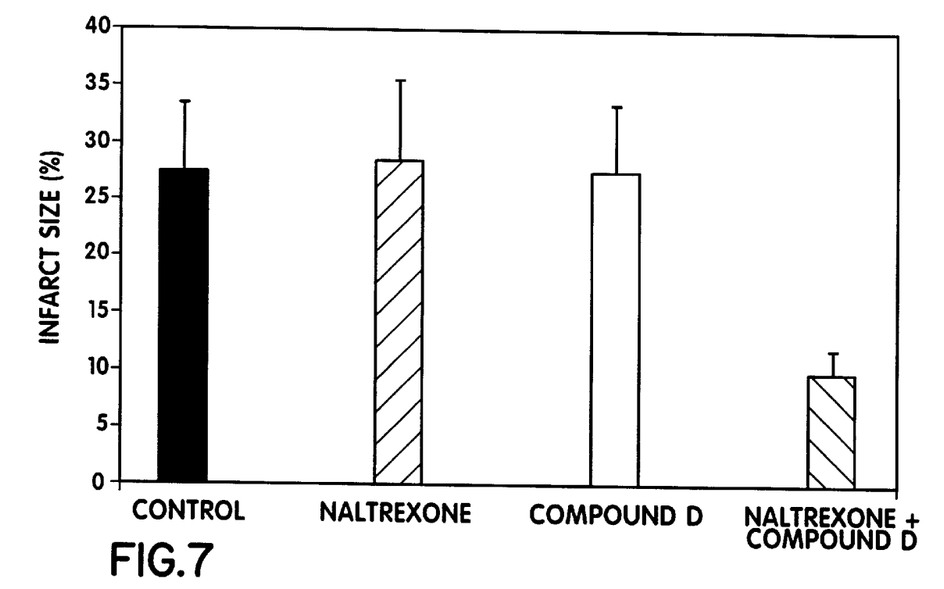
FIG. 7 is a histogram showing the effect of naltrexone on infarct size in animals pretreated with compound-D SEQ ID NO:1.

FIG. 7 shows the effect of naltrexone, a universal opioid antagonist, on infarct size. Groups of rats were pretreated 24 h prior to ischemia with either compound-D SEQ ID NO:1 at a dose of 2.0 mg/kg (n=6), naltrexone at a dose of 3 mg/kg (n=6), or a combination of compound-D SEQ ID NO:1 at a dose of 2.0 mg/kg and naltrexone at a dose of 3 mg/kg (n=6). Control rats (n=6) received vehicle (1 :1 :1 solution of 1 N NaOH:propyleneglycol:ethanol, readjusted to 7.4 with HCl) only. After 24 h pretreatment, isolated rat hearts were subjected to 20 min ischemia followed by 120 min reperfusion.

As shown in FIG. 7, these data indicate that naltrexone administered in combination with compound-D SEQ ID NO:1 did not block the cardioprotective effects of compound-D SEQ ID NO:1. In fact, the data support a synergistic cardioprotective effect from administration of a combination of compound-D SEQ ID NO:1 and naltrexone. Administration of compound-D SEQ ID NO:1 reduced infarct size from about 27% in the control group (solid bar) to about 13% in the compound-D SEQ ID NO:1 treated group (open bar) (p=0.05). The combined preischemic administration of compound-D SEQ ID NO:1 and naltrexone (downward hatched bar) red to about 10% when compared to the control group (p=0.05). Additionally, these data demonstrate that compound-D SEQ ID NO:1 does not operate via delta opioid receptors, since naltrexone, an opioid receptor antagonist, did not prevent compound-D SEQ ID NO:1 activity in reducing infarct size (about 14.5% versus about 13%, respectively).

Mouse Vas Deferens

Figure 8:
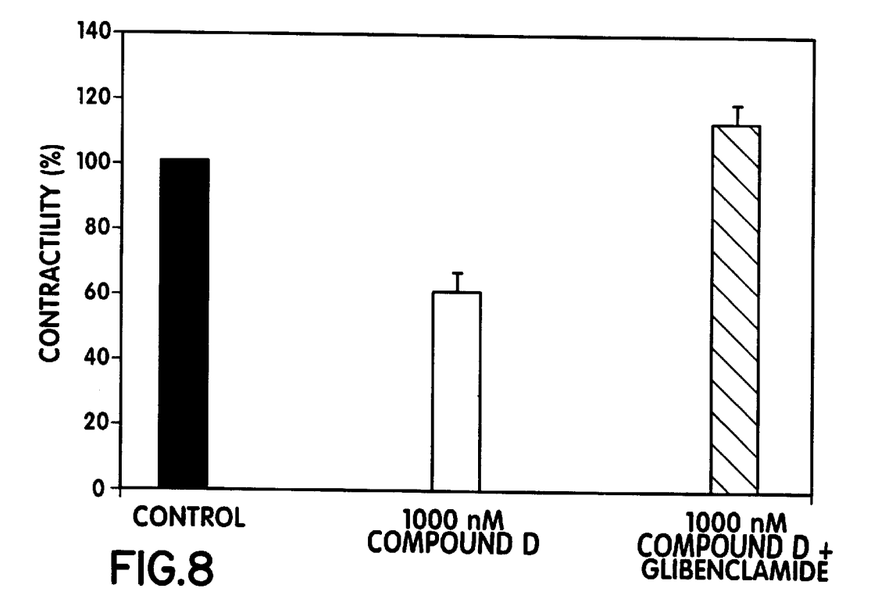
FIG. 8 is a histogram showing the effect of glibenclamide on vas deferens contractility in animals treated with 1,000 nM compound-D SEQ ID NO: 1.

Utilizing a mouse vas deferens (m.v.d.) assay, compound-D SEQ ID NO:1, it was demonstrated that opioid receptor binding requires activation and/or opening of $K_{ATP}$ channels. Glibenclamide, a $K_{ATP}$ channel blocker, blocked the inhibition of contraction of mouse vas deferens induced by compound-D SEQ ID NO:1. With reference to FIG. 8, the effect of administration of 1000 nM compound-D SEQ ID NO:1 alone (open bar) versus 1000 nM compound-D SEQ ID NO:1 with 6000 nM glibenclamide (hatched bar) on contractility of mouse vas deferens (m.v.d.) (n=6) is shown. Glibenclamide restored m.v.d. contractions which compound-D SEQ ID NO:1 had suppressed. FIG. 8 shows that 1000 nM compound-D SEQ ID NO:1 suppressed contractility to above 100%. FIG. 8 also shows that differences between control contractions and 1000 nM compound-D SEQ ID NO: 1, as well as control versus 6000 nM glibenclamide, and 1000 nM compound-D SEQ ID NO:1 versus 6000 nM glibenclamide are statistically significant.

Figure 9:
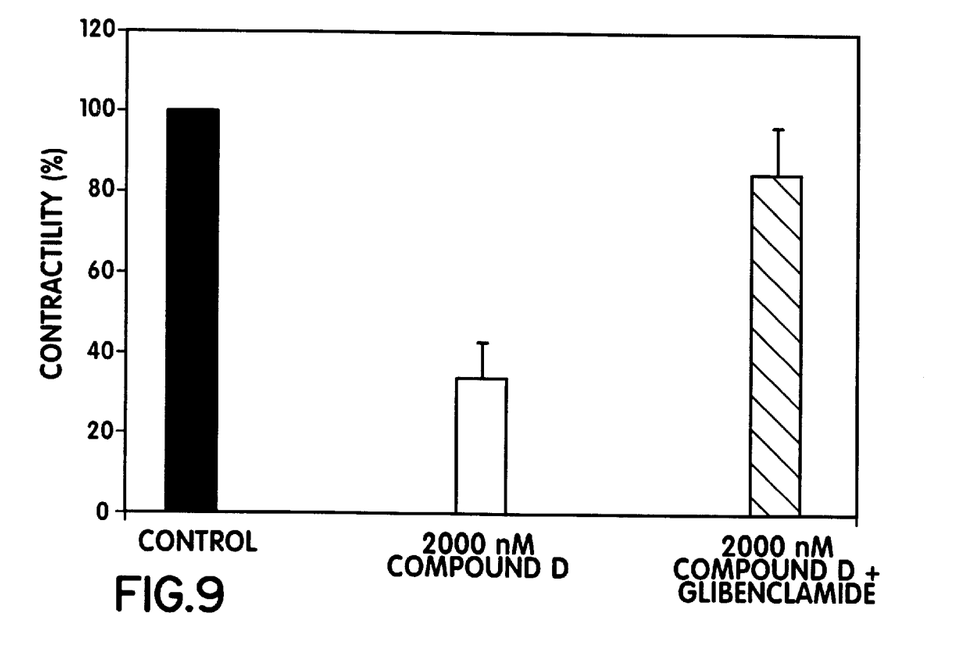
FIG. 9 is a histogram showing the effect of glibenclamide on vas deferens contractility in animals treated with 2,000 nM compound-D SEQ ID NO:1.

FIG. 9 shows the effect of administration of 2000 nM compound-D alone (open bars) versus 2000 nM compound-D SEQ ID NO:1 with 6000 nM glibenclamide (hatched bar) on contractility of m.v.d. (n=2).

These results demonstrate that the effect of compound-D SEQ ID NO:1 requires opening and/or activation of $K_{ATP}$ channels since glibenclamide, a potassium channel blocker, effectively blocked the smooth muscle inhibition of contraction induced by compound-D SEQ ID NO:1 in the m.v.d. assay. The possibility therefore exists that administration of compound-D SEQ ID NO:1 and interventions directly targeted at opening $K_{ATP}$ channels by drugs such as nicorandil or diazoxide, or anesthetics such as isoflurane, could be effective approaches for pharmacologically duplicating both short term and long term (second window) ischemic preconditioning. Thus, preinfusions of compound-D SEQ ID NO:1 may provide extended protection to the ischemic myocardium in a variety of clinical scenarios.

Compound-D, SEQ ID NO:1 has also been shown to be effective in reducing ischemic effects when administered 1 h after an episode of induced cerebral ischemia. A solution of 100 $\mu$L of either vehicle alone (control) or compound-D (treated) at a concentration of 1 mg/ml was administered either 1 h before cerebral ischemia or 1 h after cerebral ischemia (n=6 in each group). In animals receiving compound-D before ischemia, there were no significant differences in infarct volume (control 91±10 mm$^3$ versus treated 89±11 mm$^3$) or neurological score (control group 1.93±0.29 versus treated group 1.95±0.33). However, when compound-D was administered 1 h post ischemia, there were significant difference in both the infarct volume (control group 90±13 mm$^3$ versus treated group 56±9 mm$^3$) and the neurological score (control group 1.91±0.27 versus treated group 1.42±0.28) in rats receiving compound-D SEQ ID NO:1 versus the control group. The mean arterial blood pressure, $PO_2$, $pCO_2$, pH and cerebral blood flow showed no significant differences in control versus treated groups when compound-D SEQ ID NO:1 was administered either pre or post-cerebral ischemia (data not shown). These results suggest a therapeutic role for compound-D SEQ ID NO:1 in mitigating the effects of a cerebral ischemic episode that is in progress or that has occurred.

In summary, a compound that is administered to a mammal to reduce the injury associated with ischemia and reperfusion of organs such as the heart is disclosed. The compound is Tyr-D-Leu-Phe-Ala-Asp-Val-Ala-Ser-Thr-Ile-Gly-Asp-Phe-Phe-His-Ser-Ile-NH$_2$ SEQ ID NO:1. Administration prior to an ischemic event reduces tissue necrosis and preserves organ function, as measured by standard physiological indices of organ function. The compound may be administered in a time frame from 24 h up to 15 min prior to planned ischemia, or even during an ischemic period.

It should be understood that the embodiments of the present invention shown and described in the specification are only preferred embodiments of the inventors who are skilled in the art and thus are not limiting in any way. For example, compound-D SEQ ID NO:1 may be used as a protective agent for organs other than the heart. Organs isolated for transplant such as kidney, liver, lung, cornea, etc. may have enhanced viability after exposure to compound-D SEQ ID NO:1. Similarly, compound-D SEQ ID NO:1 may be administered to individuals in which ischemia to organs other than the heart has occurred or will occur. Therefore various changes, modifications or alterations to these embodiments may be made or resorted to without departing from the spirit of the invention and the scope of the following claims.

What is claimed is:

1. A composition comprising compound-D SEQ ID NO:1.

2. The composition of claim 1 wherein compound-D SEQ ID NO:1 is obtained by in vitro synthesis.

3. The composition of claim 1 wherein compound-D SEQ ID NO:1 is isolated from a natural source.

4. A solution to preserve viability of an isolated organ comprising compound-D SEQ ID NO:1 at a concentration effective to protect the organ from ischemic injury.

5. The solution of claim 3 wherein the organ is selected from the group consisting of heart, liver, kidney, cornea, lung, and combinations thereof.

6. A method of protecting against ischemia and reperfusion injury in a mammal comprising administering an effective amount of compound-D SEQ ID NO:1 to the mammal in a pharmaceutically acceptable formulation.

7. The method of claim 6 wherein administration is prior to onset of ischemia.

8. The method of claim 7 wherein administration is about 24 hours prior to onset of ischemia.

9. The method of claim 6 wherein compound-D SEQ ID NO:1 is administered as a solution.

10. The method of claim 6 wherein compound-D SEQ ID NO:1 is administered parenterally.

11. The method of claim 6 wherein compound-D SEQ ID NO:1 is administered at a concentration in the range of about 2 mg/kg of body weight of the mammal.

12. The method of claim 6 wherein compound-D SEQ ID NO:1 is administered to protect against myocardial ischemia.

13. The method of claim 2 wherein said myocardial ischemia occur during surgery.

14. The method of claim 6 wherein the formulation further includes a compound having an anti-ischemic effect.

15. The method of claim 14 wherein the compound affects nitric oxide synthase.

16. The method of claim 15 wherein the compound is arginine hydrochloride.

17. The method of claim 6 wherein compound-D SEQ ID NO:1 is administered at a concentration in the range of about 1–20 mg/kg of body weight.

18. A method to preserve at least one isolated organ comprising exposing the organ to a solution comprising a preservative and an effective amount of compound-D.

19. The method of claim 18 wherein the organ is selected from the group consisting of heart, liver, kidney, cornea, lung and combinations thereof.

20. The method of claim 18 wherein compound-D SEQ ID NO:1 is at a concentration of about 100 $\mu$M in the solution.

21. A method for reducing effects of ischemia in a mammal comprising administering an effective amount of compound-D SEQ ID NO:1 in a pharmaceutically acceptable carrier to the mammal.

22. The method of claim 21 wherein compound-D SEQ ID NO:1 is administered prior to ischemia.

23. The method of claim 21 wherein compound-D SEQ ID NO:1 is administered substantially concurrently with onset of ischemia.

24. The method of claim 21 wherein compound-D SEQ ID NO:1 is administered after one hour of cerebral ischemia.

\* \* \* \* \*

UNITED STATES PATENT AND TRADEMARK OFFICE
CERTIFICATE OF CORRECTION

PATENT NO.    : 6,316,411 B1
DATED         : November 13, 2001
INVENTOR(S)   : Oeltgen et al.

It is certified that error appears in the above-identified patent and that said Letters Patent is hereby corrected as shown below:

Column 3,
Line 19, "Tyr-D-Leu-Phe-Ala-Asp-Val-Ala-Ser-Thr-lie-Gly-Asp-Phe-Phe-His-Ser-IIe-$NH_2$" should be -- Tyr-D-Leu-Phe-Ala-Asp-Val-Ala-Ser-Thr-Ile-Gly-Asp-Phe-Phe-His-Ser-Ile-$NH_2$ --
Line 31, change "HCI" to -- HCl --
Line 62, change "NaCI" to -- NaCl --

Column 4,
Line 11, change "per centage" to -- percentage --
Line 14, change "analyze" to -- analyzed --

Column 5,
Line 18, change "troponin 1" to -- troponin l --
Line 27, change "HCI" to -- HCl --
Line 42, change "red to about" to -- reduced infarct size to about --

Column 6,
Line 38, change "pre or post-cerebral" to -- pre- or post-cerebral --

Column 7,
Line 33, change "The solution of claim 3 wherein" to -- The solution of claim 4 wherein --
Line 49, change "concentration in the range of about 2 mg/kg of body weight" to -- concentration of 2 mg/kg of body weight --
Line 54, change "The method of claim 2 wherein said myocardial ischemia occur during surgery." to -- The method of claim 12 wherein said myocardial ischemia occurs during surgery. --

Column 8,
Line 31, change "range of about 1-20 mg/kg of body weight." to -- range of 1-20 mg/kg of body weight of the mammal. --
Line 35, change "effective amount of compound-D." to -- effective amount of compound-D SEQ ID NO:1. --

UNITED STATES PATENT AND TRADEMARK OFFICE
CERTIFICATE OF CORRECTION

PATENT NO. : 6,316,411 B1
DATED : November 13, 2001
INVENTOR(S) : Oeltgen et al.

It is certified that error appears in the above-identified patent and that said Letters Patent is hereby corrected as shown below:

<u>Column 8 cont'd,</u>
Line 41, change concentration of about 100 $\mu$M" to -- concentration of 100 $\mu$M --
Line 50, change "administered substantially concurrently with onset" to -- administered with onset --

Signed and Sealed this

Tenth Day of September, 2002

Attest:

JAMES E. ROGAN
Attesting Officer    Director of the United States Patent and Trademark Office